United States Patent

Tanaka et al.

[11] Patent Number: 5,434,133
[45] Date of Patent: Jul. 18, 1995

[54] CNP ANALOG PEPTIDES AND THEIR USE

[75] Inventors: Shoji Tanaka, Hyogo; Yoshiharu Minamitake, Kanagawa; Yasuo Kitajima; Mayumi Furuya, both of Osaka; Hisayuki Matsuo, 4-24-204, Nishiokamoto 6-chome, Higashinada-ku, Kobe-shi, Hyogo-ken, all of Japan

[73] Assignees: Suntory Limited; Hisayuki Matsuo, both of Japan

[21] Appl. No.: 828,450

[22] Filed: Jan. 31, 1992

[30] Foreign Application Priority Data

Jan. 31, 1991 [JP] Japan .................. 3-011321
Jun. 28, 1991 [JP] Japan .................. 3-254066

[51] Int. Cl.⁶ ............... C07K 14/00; C07K 14/435; A61K 38/17; A61K 38/16
[52] U.S. Cl. ...................... 514/12; 514/13; 514/14; 530/324; 530/325; 530/326
[58] Field of Search ............ 530/324, 325, 326; 514/12, 13, 14

[56] References Cited

FOREIGN PATENT DOCUMENTS 0350318 10/1990 European Pat. Off. .
292256  11/1990 European Pat. Off. .
232078   4/1991 European Pat. Off. .
8912069  6/1990 WIPO .

OTHER PUBLICATIONS

Sudoh et al. Biochem. Biophys. Res. Commun. (1990) 168:863–870.
Kangawa et al. Biochem. Biophys. Res. Commun. (1984) 118:131–139.
Mayumi Furuya et al., "C–Type Natriuretic Peptide is a Growth Inhibitor of Rat Vascular Smooth Muscle Cells", Biochmical And Biophysical Research Communications, vol. 177, No. 3, 1991, Jun. 28, 1991, pp. 927–931.
Mayumi Furuya, et al. "C–Type Natriuretic Peptide Inhibits Intimal Thickening After Vascular Injury", Biochemical And Biophysical Research Communications, vol. 193, No. 1, 1993, May 28, 1993, pp. 248–253.
Chemical Abstracts, vol. 113, No. 3, Jul. 16, 1990; Chemical Abstracts, vol. 113, No. 11, Sep. 10, 1990; Chemical Abstracts, vol. 113, No. 23, Dec. 3, 1990.

Primary Examiner—Jill Warden
Assistant Examiner—Carol A. Salata
Attorney, Agent, or Firm—Cushman Darby & Cushman

[57] ABSTRACT

Novel peptides represented by the general formula:

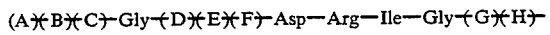

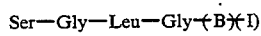

and physiologically acceptable acid addition salts thereof;

where (A) represents H-, H-Gly, H-Lys-Gly, H-Ser-Lys-Gly, H-Leu-Ser-Lys-Gly, H-Gly-Leu-Ser-Lys-Gly, H-ser, H-Ser-Ser, H-Arg-Ser-Ser, H-Arg-Arg-Ser-Ser, H-Leu-Arg-Arg-Ser-Ser, H-Ser-Leu-Arg-Arg-Ser-Ser;

(B) represents H-Cys or Pmp;

(C) represents Phe-, pCl-Phe, pF-Phe, pNO₂-Phe or Cha;

(D) represents Ile, Val, Aib, tLeu, Gly or Leu;

(E) represents Lys or Arg;

(F) represents Ile, Leu or Met;

(G) represents Ser or Ala;

(H) represents Met or Gln;

(I) represents —OH, -Asn-OH, -Asn-Ser-OH, -Asn-Ser-Phe-OH, -Asn-Ser-Phe-Arg-OH or -Asn-Ser-Phe-Arg-Tyr-OH; and the symbol " . . . " represents a disulfide bond;

provided that 1) α-hANP, 2) α-hANP (7–28) and 3) CNP-22 are excluded from the scope of that general formula.

Also disclosed are agents for suppressing the growth of vascular smooth muscle cells that contains those peptides as effective ingredients.

5 Claims, 4 Drawing Sheets

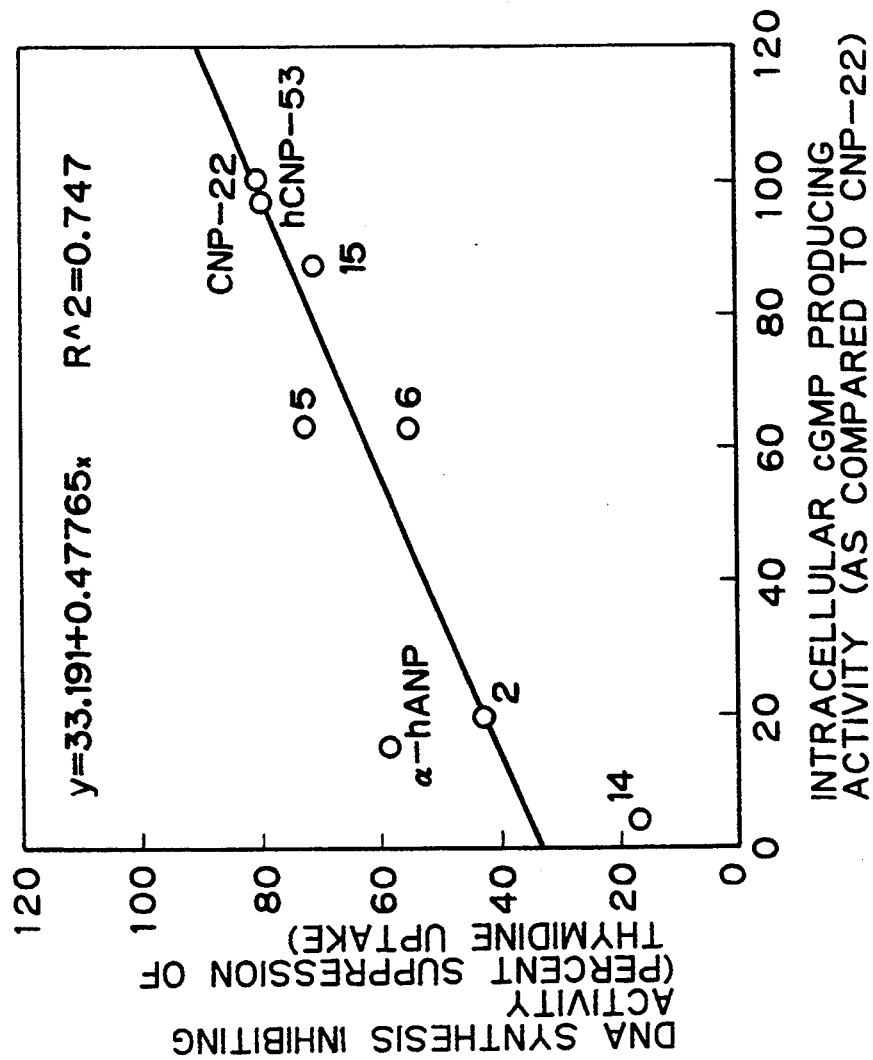

CNP ANALOG PEPTIDES AND THEIR USE

BACKGROUND OF THE INVENTION

This invention relates to the synthesis and use of peptides capable of suppressing the growth of vascular smooth muscle cells. More particularly, this invention relates to the synthesis of novel derivatives of C-type natriuretic peptide (hereunder abbreviated as "CNP"), the novel physiological actions of CNP and its derivatives, and to vascular smooth muscle cell growth suppressing agent that contains one of those peptides as an effective ingredient. The term "CNP analog derivatives" as used herein means the compound recited in appended claim 1, CNP-22, human CNP-53, porcine CNP-53, frog CNP and chick CNP.

Many peptides having natriuretic and hypotensive actions have recently been found in the hearts and brains of various animals. These peptides are collectively referred to as "natriuretic peptides" or "NPs". Many NPs having different chain lengths or similar primary amino acid sequences have heretofore been isolated and identified from living bodies and it has now become clear that all of those NPs are biosynthesized from three different NP precursor proteins (prepro ANP, prepro BNP and prepro CNP).

Therefore, NPs known today can be classified as the following three types in accordance with the route of their biosynthesis: A-type NP (A-type natriuretic peptide or ANP); B-type NP (B-type natriuretic peptide or BNP); and C-type NP (C-type natriuretic peptide or CNP).

Among these NPs, ANP and BNP were isolated from the atrium and the brain, respectively, so ANP has initially been called an atrial natriuretic peptide and BNP, a brain natriuretic peptide (Natsuo, II and Nakazato, H., Endocrinol. Metab. Clin. North Amer., 16, 43, 1987; Sudoh, T et al., Nature, 332, 78, 1988). However, later studies have revealed that ANP is produced not only in the atrium but also in the brain and that similarly, BNP is produced not only in the brain but also in the heart (Ueda, S. et al., Biochem. Biophys. Res. Commun., 149, 1055, 1987; Aburaya, M. et al., Biochem. Biophys. Res. Commun., 165, 872, 1989). It was also verified that both ANP and BNP, when administered in vivo, exhibited comparable and noticeable levels of natriuretic and hypotensive actions. On the basis of those findings, both ANP and BNP are presently considered to work not only as hormones to be secreted from the heart into blood but also as nerve transmitting factors, thereby playing an important role in maintaining the homeostatic balance of body fluid volume and blood pressure.

CNP is a group of peptides that are assignable to a third class of NPs following ANP and BNP and those peptides were isolated very recently, followed by the unravelling of their structures and the mechanism of their biosynthesis.

The first discovered CNPs were CNP-22 composed of 22 amino acid residues and CNP-53 having 31 amino acid residues attached to the N-terminus of CNP-22, and those peptides were both isolated from porcine brain and their structures were unravelled. It was also determined that CNP-22 and CNP-53 were present in nearly equal amounts in the porcine brain (Sudoh, T. et al., Biochem. Biophys. Res. Commun., 168, 863, 1990; Minamino, N. et al., Biochem. Biophys. Res. Commun., 170, 973, 1990). At a later time, porcine CNP genes and cDNA corresponding to CNP-22 and CNP-53 were isolated and their analysis has shown that both CNP-22 and CNP-53 are produced from a common precursor protein (prepro CNP). It was also found that this prepro CNP was clearly different from ANP and BNP precursor proteins (prepro ANP and prepro BNP) (Tawaragi, Y. et al., Biochem. Biophys. Res. Commun., 172, 627, 1990).

The isolation of the porcine CNP gene was followed by the isolation of rat CNP cDNA and human CNP gene and the structures of rat and human CNP precursor proteins have been unravelled. As a result, it has been found that CNP-22 has the same primary amino acid sequence in the three animal species, pig, human and rat, that CNP-53 has the same primary amino acid sequence in pig and rat but has different sequences in human and pig in that amino acid substitution occurs in two positions, and that unlike ANP and BNP, CNP is not produced in the heart but produced specifically in the brain (Kojima, M. et al., FEBS letter, 176, 209, 1990; Tawaragi, Y. et al., Biochem. Biophys. Res. Commun., 175, 645, 1991). As of today, a peptide assignable to CNP has also been isolated and identified from frogs and chicks (Japanese Patent Application Nos. 238294/1990 and 238293/1990).

Thus, it has been verified that CNP occurs not only in mammals but also in birds and amphibians. However, much is left unclear about the physiological role of CNP as NP.

The primary amino acid sequence of CNP is similar to those of ANP and BNP and, when administered in vivo, CNP exhibits natriuretic and hypotensive actions. Therefore, CNP has been held assignable to the NP family. However, compared to ANP and BNP, CNP is considerably weak in natriuretic and hypotensive actions (1/50–1/100) and, further, unlike ANP and BNP, the tissue of CNP production is limited to the brain; thus, CNP stands in a peculiar position in the NP family and it has been speculated that CNP will play other physiological roles in addition to that of maintaining the homeostatic balance of body fluid volume and blood pressure.

The studies conducted so far have shown that the mechanism by which NP exhibits a hypotensive action will probably be as follows: NP binds to an NP receptor present on the surface of a vascular smooth muscle cell, thereby increasing the level of intracellular cGMP (cyclic guanosine monophosphate), which works as an intracellular second messenger of NP to eventually cause the relaxation of blood vessels. As a matter of fact, it has been verified that the level of intracellular cGMP rises when NP is allowed to act on a sample of blood vessel or cultured vascular smooth muscle cells (VSMC).

However, the present inventors recently found that when CNP was allowed to act on VSMC, it unexpectedly increased the level of intracellular cGMP in VSMC several times as much as in the case where ANP or BNP was used (Furuya, M. et al., Biochem. Biophys. Res. Commun., 170, 201, 1990). This suggests that cGMP induced by CNP not only works as a second messenger in vascular relaxation but also has a capacity for functioning as a mediator in the development of other physiological actions. In this regard, Garg et al. have shown that vascular relaxants such as nitroprruside and S-nitroso-N-acetyl penillamine suppress cell growth in a rat VSMC line and that 8-bromo cGMP exhibits a similar action in the same cell line. Garg et al. have concluded that this growth suppressing action is caused by cGMP induced by nitric oxide (NO) radicals (Garg, U. C. et al., J. Clin. Invest., 83, 1774, 1989).

Kariya et al. have reported that ANP enhances the production of intracellular cGMP in cultured vascular smooth muscle cells derived from rabbit aortas, thereby suppressing the growth of those cells (Kariya, K. et al., Atherosclerosis, 80, 143, 1989).

All the reports mentioned above suggest strongly that cGMP works as a mediator in suppressing the growth of cultured vascular smooth muscle cells and they also suggest the possibility that cGMP induced by CNP also suppresses the growth of cultured vascular smooth muscle cells. However, it is not known today whether CNP suppresses the growth of cultured vascular smooth muscle cells.

On the other hand, it is known that all NPs have a cyclic structure composed of 17 amino acid residues that are formed on the basis of intramolecular S—S bonds. Thus, when the structure of NP is divided into three domains including the common cyclic structure (i.e., an exocyclic N-terminal domain, an endocyclic domain, and an exocyclic C-terminal domain), it can be seen that the structure of CNP differs from those of ANP and BNP in the following points (see FIG. 1). First, the primary amino acid sequence of CNP completely differs from that of ANP or BNP in terms of the exocyclic N-terminal domain whereas the endocyclic domain of CNP differs from that of ANP in terms of 5 of the 17 amino acid residues and differs from that of BNP in terms of 4 of the 17 amino acid residues. The structure of the exocyclic C-terminal domain of CNP differs greatly from that of ANP or BNP since it does not have the "tail" structure which occurs in ANP or BNP (in the case of ANP and BNP, 5 or 6 amino acids are attached to the C-terminal side of the cyclic structure of ANP or BNP, respectively, and this structure is named a "tail" structure for the sake of convenience). Obviously, these structural differences between CNP and ANP or BNP contribute to the development of the aforementioned characteristic physiological actions of CNP. However, it has not yet been known as to which domain structure of CNP and which primary amino acid sequence are directly involved in the strong cGMP producing activity of CNP.

SUMMARY OF THE INVENTION

A first object, therefore, of the present invention determines as to whether peptides assignable to CNP isolated from the nature will suppress the growth of cultured vascular smooth muscle cells.

A second object of the present invention is to unravel the minimum activity structure of CNP that contributes to the development of its strong cGMP producing activity, as well as the primary sequence of the essential amino acids of CNP. On the basis of the thus obtained findings, the present invention aims at constructing novel CNP derivatives that exhibit a stronger cGMP producing activity than naturally derived CNP.

A third object of the present invention is to find a method of using naturally derived CNP and its derivatives as pharmaceutical drugs.

To begin with, in order to achieve the first object of the invention, the present inventors checked to see whether or not CNP would suppress the DNA synthesis of cultured rat vascular smooth muscle cells stimulated with sera or PDGF (platelet derived growth factor).

Then, in order to achieve the second object of the invention, the present inventors constructed those derivatives of α-hANP (in humans, this peptide is primarily secreted from the atrium into blood) and CNP-22 in which part of the amino acid sequences were interchanged with each other, as well as a CNP-22 derivative from which the exocyclic N-terminal domain was deleted, and established which domain or primary amino acid sequence of CNP would contribute to the development of the strong cGMP producing activity which was characteristic of CNP. At the same time, the present inventors unravelled the minimum activity structure which was necessary for the development of the aforementioned activity of CNP. The present inventors then replaced some amino acid residues in those CNP derivatives by unusual amino acid (non-native type) residues so as to construct CNP derivatives that had a stronger cGMP producing activity and DNA synthesis inhibiting activity than CNP.

In order to achieve the third object of the invention, the present inventors entirely reviewed the previously known physiological actions of CNP including those disclosed by the present invention, as well as the observations heretofore obtained on the basis of the analyses of various diseased tissues and thereby present a specific method of using CNP and novel CNP derivatives as pharmaceutical drugs.

BRIEF DESCRIPTION OF THE DRAWINGS

FIG. 4 is a graph showing the correlation between the cGMP producing activity and DNA synthesis inhibiting activity of CNP analog peptides.

DETAILED DESCRIPTION OF THE INVENTION

Figure 2:
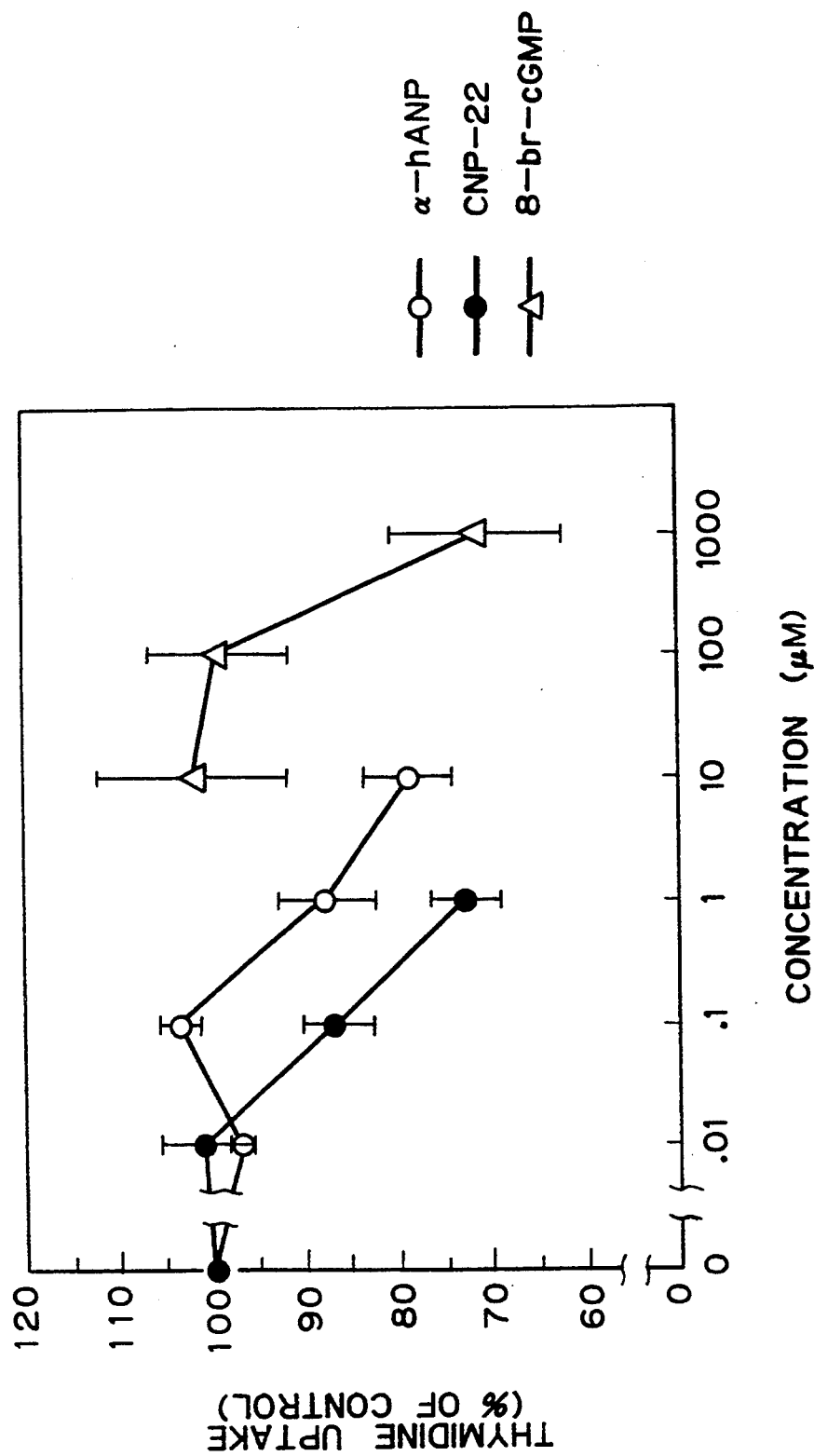
FIG. 2 is a graph showing the DNA synthesis inhibiting action of α-hANP and CNP-22.
Figure 3:
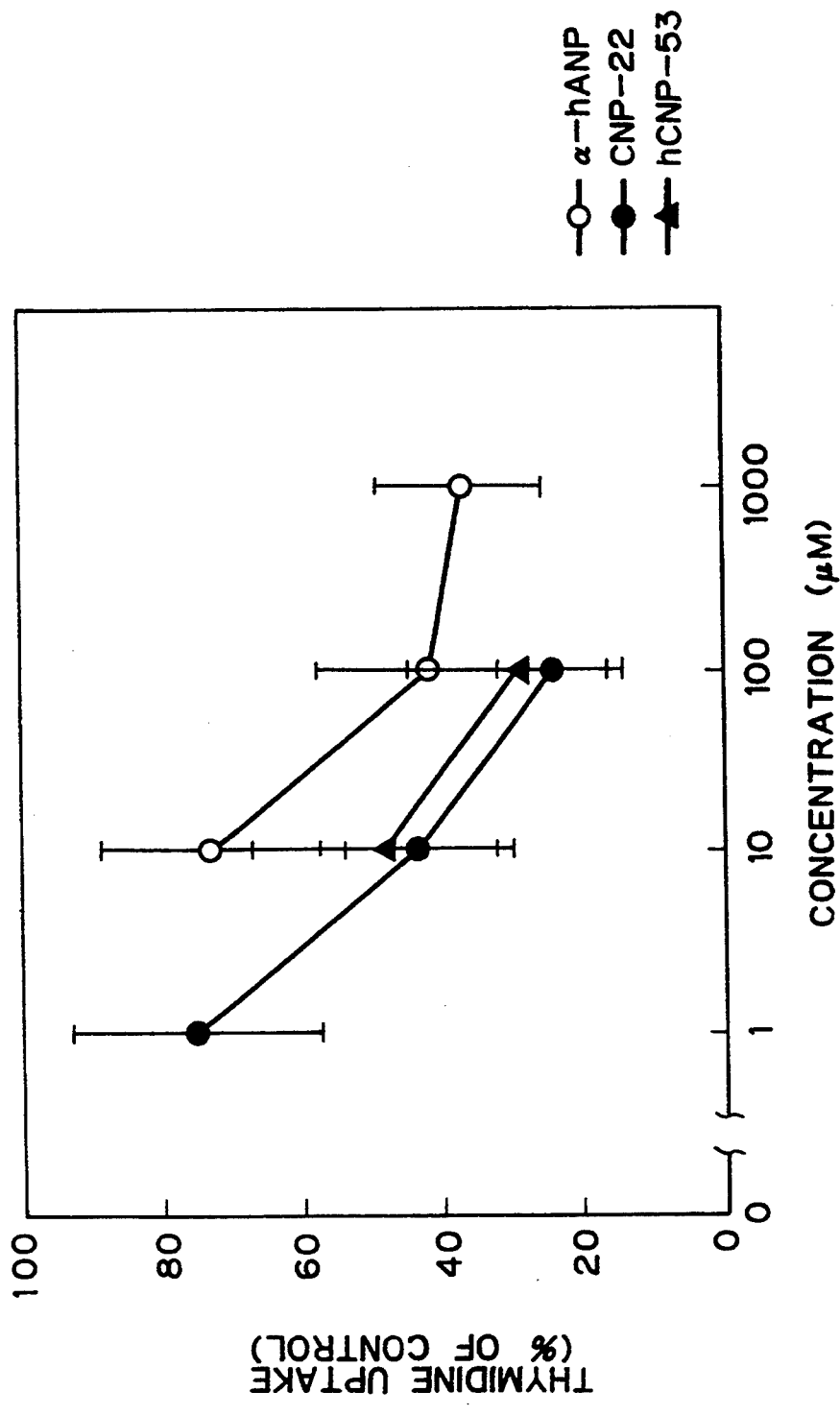
FIG. 3 is a graph showing the DNA synthesis inhibiting action of α-hANP, CNP-22 and hCNP-53.

In accordance with the method described in Example 1 under 1-2 (see below), the present inventors made an investigation to see whether CNP-22 and human CNP-53 (hCNP-53) would suppress the cell growth of rat VSMC. It was found that as shown in FIGS. 2, 3 and 4, both CNP-22 and hCNP-53 would suppress the DNA synthesis of rat VSMC in a dose-dependent manner and with a comparable intensity. It was also found that the intensity of their action was 10 times as great as α-hANP. Further, it was found that as shown in Table 1 below, CNP-22 suppressed the increase in the cell count of VSMC as stimulated with serum.

TABLE 1

Suppression by CNP-22 and α-hANP of the growth of rat vascular smooth muscle cells stimulated with 1% serum

| Compound | Dose | Cell count ($\times 10^3$ cells/well) | [% of control] |
|---|---|---|---|
| Physiological saline | | 20.6 ± 0.2 | [100] |
| CNP-22 | $5 \times 10^{-7}$M | 15.0 ± 0.3* | [72.8 ± 1.1] |

TABLE 1-continued

Suppression by CNP-22 and α-hANP
of the growth of rat vascular
smooth muscle cells stimulated
with 1% serum

| Compound | Dose | Cell count ($\times 10^3$ cells/well) | [% of control] |
|---|---|---|---|
| α-hANP | $5 \times 10^{-7}$M | $17.1 \pm 0.2$** | [$83.0 \pm 1.3$] |

Data shown as mean ± s.d. (n = 12)
*: $p < 0.01$, with statistically significant difference in Student's t-test.
**: $p < 0.05$, with statistically significant difference in Student's t-test.

On the basis of the data shown above, it was discovered for the first time that CNPs (CNP-22 and hCNP-53) exhibited the ability to suppress the cell growth of rat VSMC. It was also found that a positive correlation existed between the intensity of their ability to suppress cell growth and the concentration of intracellular cGMP.

The present inventors then constructed various CNP derivatives in accordance with the guideline to be described below and made an investigation as to which structure or primary amino acid sequence of CNP would be responsible for the strong cGMP producing activity characteristic of CNP.

Figure 1:
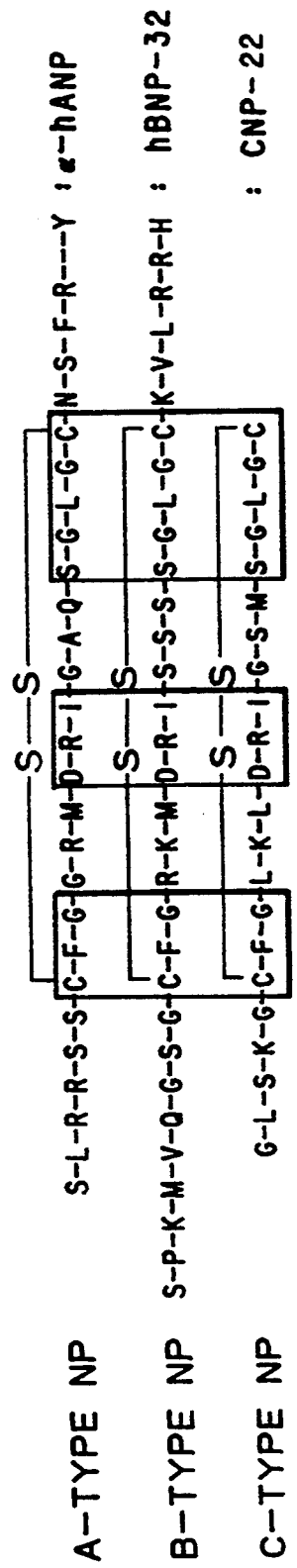
FIG. 1 is a diagram showing the primary structures of representative natriuretic peptides that belong to the respective classes of A-type NP, B-type NP and C-type NP (see SEQ ID NOs: 40–42)

As already mentioned, structural comparison of CNP-22 with α-hANP as regards three domains (exocyclic N-terminal domain, endocyclic domain, and exocyclic C-terminal domain) shows that CNP-22 differs from α-hANP in the following points (see FIG. 1). First, the primary amino acid sequence of CNP-22 differs entirely from α-hANP in terms of the exocyclic N-terminal domain and as regards the endocyclic domain, CNP-22 differs from α-hANP in five out of the 17 amino acid residues (9-position leucine, 10-position lysine, 11-position leucine, 16-position serine and 17-position methionine residues in GNP-22, provided that those residues correspond to 10-position glycine, 11-position arginine, 12-position methionine, 17-position alanine and 18-position glutamine residues in α-hANP). Further, GNP-22 does not have the exocyclic C-terminal domain which is present in α-hANP. Therefore, it is obvious that these structural differences are responsible for the differences in physiological action between CNP and ANP (especially the difference in cGMP-producing activity against VSMC).

Under these circumstances, the present inventors conducted investigations to determine which domain structure of GNP was responsible for the cGMP producing activity characteristic of CNP. Table 2 below shows the primary structures of all the derivatives synthesized in accordance with the present invention (see SEQ ID NOs: 1-29).

TABLE 2

Amino acid sequence of novel CNP derivatives

| Compound No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| (α-hANP): | S | L | R | R | S | S | C | F | G | G | R | M | D | R | I | G | A | Q | S | G | L | G | C | N | S | F | R | Y |
| (CNP-22): Residual No. |  | 1 | 2 | 3 | 4 | 5 | 6 | 7 | 8 | 9 | 10 | 11 | 12 | 13 | 14 | 15 | 16 | 17 | 18 | 19 | 20 | 21 | 22 |  |  |  |  |  |
| (CNP-22): |  | G | L | S | K | G | C | F | G | L | K | L | D | R | I | G | S | M | S | G | L | G | C |  |  |  |  |  |
| 1 | S | L | R | R | S | S | C | F | G | G | R | M | D | R | I | G | A | Q | S | G | L | G | C | N | S | F | R | Y |
| 2 |  | G | L | S | K | G | C | F | G | L | K | L | D | R | I | G | A | Q | S | G | L | G | C |  |  |  |  |  |
| 3 |  | G | L | S | K | G | C | F | G | L | K | L | D | R | I | G | S | M | S | G | L | G | C |  |  |  |  |  |
| 4 | S | L | R | R | S | G | C | F | G | L | K | L | D | R | I | G | A | Q | S | G | L | G | C |  |  |  |  |  |
| 5 |  | G | L | S | K | G | C | F | G | L | K | L | D | R | I | G | S | M | S | G | L | G | C |  |  |  |  |  |
| 6 |  | G | L | S | K | G | C | F | G | G | K | L | D | R | I | G | S | M | S | G | L | G | C |  |  |  |  |  |
| 7 |  | G | L | S | K | G | C | F | G | L | R | L | D | R | I | G | S | M | S | G | L | G | C |  |  |  |  |  |
| 8 |  | G | L | S | K | G | C | F | G | L | K | M | D | R | I | G | S | M | S | G | L | G | C |  |  |  |  |  |
| 9 |  | G | L | S | K | G | C | F | G | L | K | L | D | R | I | G | S | M | S | G | L | G | C |  |  |  |  |  |
| 10 |  | G | L | S | K | G | C | F | G | L | K | L | D | R | I | G | S | Q | S | G | L | G | C |  |  |  |  |  |
| 11 |  | G | L | S | K | G | C | F | G | L | K | L | D | R | I | G | S | M | S | G | L | G | C |  |  |  |  |  |
| 12 |  | G | L | S | K | G | C | F | G | L | R | M | D | R | I | G | S | M | S | G | L | G | C |  |  |  |  |  |
| 13 |  | G | L | S | K | G | C | F | G | L | R | L | D | R | I | G | S | M | S | G | L | G | C |  |  |  |  |  |
| 14 |  | G | L | S | K | G | C | F | G | L | R | M | D | R | I | G | S | M | S | G | L | G | C |  |  |  |  |  |
| 15 | S | L | R | R | S | S | C | F | G | L | K | L | D | R | I | G | A | Q | S | G | L | G | C | N | S | F | R | Y |
| 16 |  | G |  |  | K | G | C | pClF | G | L | K | L | D | R | I | G | S | M | S | G | L | G | C |  |  |  |  |  |
| 17 |  | G |  |  |  |  | PmP | F | G | L | K | L | D | R | I | G | S | M | S | G | L | G | C |  |  |  |  |  |
| 18 |  | G |  |  |  |  | PmP | pClF | G | L | K | L | D | R | I | G | S | M | S | G | L | G | C |  |  |  |  |  |
| 19 |  | G |  |  |  |  | MeC | F | G | L | K | L | D | R | I | G | S | M | S | G | L | G | MeC |  |  |  |  |  |
| 20 |  | G | L | S | K | G | C | F | G | L | K | L | D | R | I | G | S | M | S | G | L | G | C |  |  |  |  |  |
| 21 |  | G | L | S | K | G | C | F | G | V | K | L | D | R | I | G | S | M | S | G | L | G | C |  |  |  |  |  |
| 22 |  | G | L | S | K | G | C | F | G | Aib | K | L | D | R | I | G | S | M | S | G | L | G | C |  |  |  |  |  |
| 23 |  | G | L | S | K | G | C | F | G | tL | K | L | D | R | I | G | S | M | S | G | L | G | C |  |  |  |  |  |
| 24 |  | G | L | S | K | G | C | pClF | G | L | K | L | D | R | I | G | A | Q | S | G | L | G | C | N | S | F | R | Y |
| 25 |  | G | L | S | K | G | C | pFF | G | L | K | L | D | R | I | G | A | Q | S | G | L | G | C | N | S | F | R | Y |
| 26 |  | G | L | S | K | G | C | pNO2F | G | L | K | L | D | R | I | G | A | Q | S | G | L | G | C | N | S | F | R | Y |
| 27 |  | G | L | S | K | G | C | cha | G | L | K | L | D | R | I | G | A | Q | S | G | L | G | C | N | S | F | R | Y |

First, the inventors synthesized an α-hANP derivative having the exocyclic C-terminal domain deleted, CNP-22 and α-hANP derivatives having the respective domains interchanged therebetween, and a CNP-22 derivative having the exocyclic N-terminal domain deleted (see Table 2 under 1–5), and they investigated the cGMP producing activity of those derivatives.

As shown in Table 3 below, it was found that each of derivatives 3 and 4 which had the endocyclic domain structure of CNP-22 in their molecule, and derivative 5 which had the exocyclic N-terminal domain of CNP-22 deleted exhibited a strong cGMP producing activity at a comparable level to that exhibited by CNP-22.

TABLE 3

| | Physiological activities of CNP analogs | |
|---|---|---|
| Compound | % Inhibition of $3_H$-thymidine uptake[1] | cGMP producing activity (% increase for 1 μm)[2] |
| α-hANP | 58 | 100 |
| CNP-22 | 76 | 621 |
| 1 | NT | 62 |
| 2 | 38 | 147 |
| 3 | NT | 667 |
| 4 | NT | 663 |
| 5 | 65 | 616 |
| 6 | 49 | 344 |
| 7 | NT | 413 |
| 8 | NT | 497 |
| 9 | NT | 707 |
| 10 | NT | 659 |
| 11 | NT | 71 |
| 12 | NT | 273 |
| 13 | NT | 58 |
| 14 | 17 | 23 |
| 15 | 72 | 559 |
| 16 | NT | 688 |
| 17 | NT | 233 |
| 18 | NT | 333 |
| 19 | NT | 38 |
| 20 | NT | 499 |
| 21 | NT | 549 |
| 22 | NT | 160 |
| 23 | NT | NT |
| 24 | NT | 719 |
| 25 | NT | 785 |
| 26 | NT | 255 |
| 27 | NT | 523 |
| hCNP-53 | 71 | 458 |
| pCNP-53 | NT | 524 |

[1] Percent inhibition as achieved by adding 0.1 μm of each peptide to a BSMC line stimulated with PDGF (20 ng/ml).
[2] Specific activity as compared to the activity of 1 μm α-hANP (2000 fmol/400000 cells), with maximum activity being equivalent to the cGMP producing ability of each compound for 1 μm.

On the other hand, derivative 1 having the exocyclic C-terminal domain of α-hANP deleted and derivative 2 in which the exocyclic N-terminal domain of α-hANP was replaced by the exocyclic N-terminal domain of CNP-22 were found to exhibit only a weak cGMP producing activity at a level comparable to α-hANP.

On the basis of the data described above, it was concluded that the strong cGMP producing activity of CNP was due to the endocyclic domain structure of CNP-22. Further, it was eventually found that derivative 19 which had the intramolecular S—S bonds of CNP-22 cleaved hardly reduced the cGMP producing activity and this fact enabled the present inventors to conclude that cyclic CNP (6–23) 5 was the minimum activity structure regarding the cGMP producing activity of CNP.

Subsequently, the present inventors made an investigation as to which of the amino acid residues (or which primary amino acid residue) in the endocyclic domain of CNP was important for the development of the cGMP producing activity of CNP. To this end, using CNP-22 as the skeletal structure, the present inventors constructed one-residue substituted derivatives (see Table 2 under 6–10) in which 5 amino acid residues in the endocyclic domain of CNP-22 that were different than α-hANP (i.e., 9-position leucine, 10-position lysine, 11-position leucine, 16-position serine and 17-position methionine residues) were replaced by the corresponding amino acid residues in α-hANP (i.e., 10-position glycine, 11-position arginine, 12-position methionine, 17-position alanine and 18-position glutamine), and their activity for cGMP production was investigated.

As shown in Table 3, both derivatives 9 (16-position substituted derivative of CNP-22) and 10 (17-position substituted derivative) exhibited a strong activity comparable to that of CNP-22. On the other hand, derivatives 6, 7 and 8 (9-, 10- and 11-position substituted derivatives, respectively, of CNP-22) had a lower activity than CNP-22 (but higher than that of α-hANP).

On the basis of these data, it was found that the 9-position leucine, 10-position lysine and 11-position leucine residues of CNP-22 were important for the development of the cGMP producing activity of CNP. However, as is clear from Table 3, none of the one-residue substituted derivatives (6, 7 and 8) achieved satisfactory reduction in activity; therefore, it was anticipated that the residues important to the activity were not single residues but that they would be composed of at least two residues selected from among the 9-position leucine, 10-position lysine and 11-position leucine residues of CNP-22.

Therefore, the present inventors subsequently constructed two-residue substituted derivatives (see Table 2 under 11–13) and three-residue substituted derivative (see Table 2 under 14) by combining the 9-position leucine, 10-position lysine and 11-position leucine residues of CNP-22 and investigated their cGMP producing activity.

As shown in FIG. 3, the three-residue substituted derivative 14 caused a marked drop in activity as was expected. Each of the two-residue substituted derivatives caused an even greater drop in activity than the aforementioned one-residue substituted derivatives. The drop in activity caused by derivatives 11 and 13 was particularly marked.

On the basis of those analyses, it was found that Leu-Lys-Leu, namely, the sequence of positions 9 to 11 of the primary amino acid sequence for the endocyclic domain of CNP-22 was important for the development of the cGMP producing activity of CNP. This was also verified by the fact that three-residue substituted derivative 15 in which the amino acid residues in positions 10, 11 and 12 of α-hANP were replaced by leucine, lysine and leucine residues, respectively, exhibited a strong cGMP producing activity at a substantially comparable level to CNP-22. It is difficult to identify which of the three-residues in positions 9–11 of CNP-22 is particularly important on the basis of the above-described experimental results but in view of the fact that the one-residue substituted derivative 6 and the two-residue substituted derivatives 11 and 13 were all lower in cGMP producing activity than the other one- and two-residue substituted derivatives, the leucine residue in position 9 of CNP may well be considered to be particularly important. In other words, the difference in cGMP producing ability between ANP and CNP would originate from the difference between the leucine residue in position 9 of CNP-22 and the corresponding glycine residue in position 10 of α-hANP.

In the next place, combining those findings of the present invention with the observations obtained by the previous studies on the structure-activity correlation of ANP (see, for example, Minamitake, Y. et al., Biochem. Biophys. Res. Commun., 172, 971, 1990), the present inventors attempted to prepare CNP derivatives having a stronger cGMP producing activity and DNA synthesis inhibiting activity than naturally occurring NP (ANP or CNP).

First, noting the leucine residue in position 9 of CNP-22, the present inventors constructed derivatives that had CNP-22 as the skeletal structure and in which the leucine residue in position 9 was replaced by isoleucine, valine, α-aminoisobutyric acid or t-leucine residue (see Table 2 under 20–23). Then, the inventors constructed other derivatives that had CNP (6–22) 5 as the skeletal structure and in which the cysteine residue in position 6 was replaced by a pentacyclomercaptopropionyl group, the phenylalanine residue in position 7 was replaced by a p-chloro-phenylalanine residue, and the 6- and 7-position residues were respectively replaced by pentacyclomercaptopropionyl and p-chloro-phenylalanine residues (see Table 2 under 16, 17 and 18). Further, the inventors constructed other derivatives that had [Leu10, Lys11, Leu12] α-hANP (7–28) as the skeletal structure and in which the phenylalanine residue in position 8 was replaced by p-chloro-phenylalanine, p-fluoro-phenylalanine, p-nitro-phenylalanine and cyclohexylalanine residues, respectively (see Table 2 under 24–27). The inventors also investigated the cGMP production by those derivatives.

As shown in Table 3, among the derivatives having CNP-22 as the skeletal structure, derivatives 20 and 21 were found to exhibit substantially the same level of activity as CNP-22. As for the derivatives having CNP (6–22) as the skeletal structure, derivative 16 was found to exhibit a stronger activity than CNP-22. As regards the derivatives having [Leu10, Lys11, Leu12] α-hANP (7–28) as the skeletal structure, derivatives 15, 24, 25 and 27 were found to exhibit 4–6 times as high activity as α-hANP. Derivatives 24 and 25 were found to have a particularly high activity, even stronger than CNP-22.

On the basis of these results, it was found that derivatives exhibiting a stronger cGMP producing activity than CNP-22 or α-hANP could be constructed by replacing part of the amino acid residues in CNP-22, CNP (6–22) and [Leu10, Lys11, Leu12] α-hANP (7–28) with unusual amino acid (non-native type) residues.

We now describe specifically the method of using CNP and its derivatives as pharmaceutical drugs.

Up to date, there have been reported various disease caused by the abnormal growth of vascular smooth muscle cells. For example, the restenosis of the coronary artery occurs in about 30% of the patients on whom percutaneous transluminal coronary angioplasty (PTCS) has been performed successfully and it is known that in almost all cases, the cause is not the formation of thrombi but the abnormal growth of arterial smooth muscle cells. it is also known that restenosis of a similar type occurs in blood vessels in transplanted tissues including an artery bypass. Further, the growth of vascular smooth muscle cells has often been found in the blood vessels of patients suffering from arteriosclerosis. However, no therapeutics have yet been found that are effective against those diseases due to the growth of vascular smooth muscle cells and their development is presently in demand.

In the present invention, the inventors have revealed for the first time that CNP is capable of effectively suppressing the growth of vascular smooth muscle cells. The inventors have also revealed that a positive correlation holds between the intensity of this action and that of cGMP producing activity. Further, the inventors succeeded in constructing derivatives exhibiting a stronger cGMP producing activity than naturally occurring ANP or CNP.

With these facts taken together, CNP and its derivatives that exhibit a strong cGMP producing activity against vascular smooth muscle cells can potentially be used as effective therapeutics or preventives against diseases such as restenosis and arteriosclerosis that are caused by the abnormal growth of vascular smooth muscle cells.

To summarize, the present inventors unravelled the fact that CNP strongly suppresses the abnormal growth of vascular smooth muscle cells and further found that a positive correlation would hold between the intensity of this action and that of cGMP producing activity.

The present inventors then synthesized various novel derivatives of CNP and found that CNP (6–22) was the minimum structure required for the cGMP producing activity of CNP against VSMC. The present inventors also succeeded in synthesizing novel CNP derivatives that would exhibit a stronger cGMP producing activity than naturally occurring ANP or CNP. Further, the present inventors found that CNP and its derivatives could be used as effective therapeutics or preventives against diseases such as restenosis and arteriosclerosis that are caused by the abnormal growth of vascular smooth muscle cells. The present invention has been accomplished on the basis of those findings.

In specific examples of the present invention, the description concerns the CNP derivatives listed in Table 2 but it should be noted that in the light of the findings of the present invention, the construction of derivatives exhibiting a stronger cGMP producing activity against VSMC is also applicable to the other NPs the structures of which have already been identified.

The peptides of the present invention may be converted to acid addition salts with inorganic acids such as hydrochloric acid, sulfuric acid and phosphoric acid, or with organic acids such as formic acid, acetic acid, butyric acid, succinic acid and citric acid.

The peptides of the present invention can be produced by standard methods of chemical synthesis or recombinant DNA techniques (except for derivatives that contain amino acid residues of a non-native type). Review books on methods of chemical synthesis include, for example, "Seikagaku Jikken Koza (A Course in Experimental Biochemistry) I, Tanpakushitsu no Kagaku (Protein Chemistry), IV, Part II, pages 207–495" published by Tokyo Kagaku Dojin, "Peputido Gosei no Kiso to Jikken (Fundamentals and Experiments of Peptide Synthesis), by N. Izumiya et al.", published by Maruzen, and "Peputido Kemisutori (Peptide Chemistry), 1984, pp. 229–234, pp. 235–240 and pp. 241–246, ed. by Izumiya" ed. by Izumiya", published by Tanpakuken (Protein Engineering Research Laboratory), and various methods of synthesis are described in detail in those books. An example of the production methods by recombinant DNA techniques is described in "Idenshi Sosa (Gene Manipulation), 1990, Extra Issue of Tanpakushitsu Kakusan Koso (Proteins, Nucleic Acid and Enzymes), pages 2613–2619, ed. by M. Takanami and K. Kimura", published by Kyoritsu Shuppan, and the basic procedures of production are described in this reference.

The peptides of the present invention were synthesized in accordance with the method of chemical synthesis described in those references. Namely, amino acids with protective groups were condensed and extended by a method known as the solid-phase method" and, after removing all protective groups with hydrogen fluoride, the desired peptides were produced via a disulfide binding reaction.

The crude peptides obtained by the aforementioned methods are purified by combinations of common methods of purification such as ion-exchange column chromatography, reverse-phase column chromatography, etc.

The pharmaceutical composition of the present invention can be administered either as free forms of the peptides of the present invention or as pharmacologically acceptable acid addition salts thereof.

The peptides of the present invention or their pharmacologically acceptable acid addition salts are desirably mixed with a pharmacologically acceptable carrier, excipient, diluent, etc. that are known per se before they are administered by methods that are commonly used with peptide drugs, namely, by parenteral administration such as intravenous, intramuscular or subcutaneous administration. However, they may be administered perorally as microcapsules in which the peptides of the present invention are incorporated as the active ingredient in liposome, polyamide, etc. and which are rendered resistant to degradation in the digestive tract. Another method of administration that can be adopted is to have the drug absorbed through the mucous membrane such as in the rectum, within the nose or eye or beneath the tongue, so that the drug is administered as a suppository, intranasal spray, eye drop or sublingual tablet.

The dose of the pharmaceutical composition of the present invention may vary with the kind of disease, the age of patient, his body weight, the severity of disease, the route of administration, etc.; typically, it can be administered in a daily dose of 0.01–10 mg/body, with the preferred range being from 0.05 to 1 mg/body.

Unless otherwise noted, the amino acids mentioned herein are in L-form and the abbreviations for those amino acids and reagents are listed below.

Asp: L-asparagine
Asp(OcHex): β-cyclohexylaspartic acid
Ser: L-serine
Ser(Bzl): 0-benzyl-L-serine
Gln: L-glutamine
Gly: Glycine
Ala: L-alanine
Cys: L-cysteine
Cys(4MeBzl): 4-methylbenzyl-L-cysteine
Met: L-methionine
Ile: L-isoleucine
Leu: L-leucine
t-Leu: L-tertiary leucine
Tyr: L-tyrosine
Tyr(BrZ): 0-2-bromobenzyloxycarbonyl-L-tyrosine
Phe: L-phenylalanine
Arg: L-arginine
Arg(Tos): G-tosyl-L-arginine
pClPhe: parachloro-L-phenylalanine
Pmp: pentacyclomercaptopropionic acid
Aib: aminoisobutyric acid
Lys: L-lysine
Boc-: t-butyloxycarbonyl
TFA: trifluoroacetic acid
NMP: N-methylpyrrolidone
DMSO: dimethyl sulfoxide
HOBt: N-hydroxybenzotriazole
DIEA: diisopropylethylamine
DCC: dicyclohexylcarbodiimide The purity of each final product was assayed by the procedures of thin-layer chromatography, analytical high-performance liquid chromatography and amino acid analysis that are described below.

Thin-layer Chromatography

Support: silica gel 60 F-254 (Merck)
Developing solvent:
  rf1 n-butanol:acetic acid:pyridine:water=4:1:1:2
  rf2 n-butanol:acetic acid:pyridine:water=30:20:6:24

Analytical High-performance Liquid Chromatography

Apparatus: Shimadzu LC-6A system
Column: YMC-Pack A-302 0D5 4.6$^{-\phi}$×150 mm
Developing solvent: 30-min linear gradient from 18% $CH_3CN$/0.1% TFA to 60% $CH_3CN$/0.1% TFA Amino Acid Analysis Apparatus: Hitachi Amino Acid Analyzer Model 835

The following examples are provided for the purpose of further illustrating the present invention but are in no way to be taken as limiting.

EXAMPLE 1

Measurements of Biological Activities 1-1: Measurement of CGMP Producing Activity The above-mentioned activity of compounds synthesized according to the present invention was measured by the methods of Hirata et al. (Biochem. Biophys. Res. Commun., 128, 538, 1985) and Scarborough et al. (J. Biol. Chem., 261, 12960, 1986). The cells used were cultured vascular smooth muscle cells (hereunder abbreviated as VSMC) derived from the aortas of rats. From $10^{-9}$ to $10^{-6}$M of α-hANP or a 20 peptide of interest was incubated together with VSMC and the amount cGMP produced was measured by cGMP radioimmunoassay. Percent maximum reactivity for each peptide, with the value of maximum reactivity for α-hANP being taken as 100%, was used as an indicator of activity.

1-2: Measurement of Cell Growth Suppressing Activity

Cell growth suppressing activity was evaluated in accordance with the method of Kariya et al. (Atherosclerosis, 80, 143–147, 1990) by measuring the uptake of [$^3$H] thymidine into cells as an indicator of percent DNA synthesis inhibition using the above-identified VSMC. Cells tuned to a stationary phase were incubated at 37° C. for 14 h with each sample added in the presence of 1% serum or 20 ng/ml of PDGF (platelet derived growth factor). Then, following the addition of 37 kBq/ml of [$^3$H] thymidine, the incubation was continued for another 4 h and the radioactivity of [$^3$H] thymidine incorporated into the cells was measured. The values of measurement were such that the uptake of [$^3$H] thymidine for the case where only 1% serum or PDGF was added in the absence of peptide was taken as 100%, with the percent suppression due to the peptide addition being accordingly calculated. The results of measurements are shown in FIGS. 2 and 3 and in Table 3.

As for CNP-22, VSMC were cultured for 4 days in the presence of 1% serum with CNP-22 or α-hANP being added, and the number of cells was counted with a hemocytometer. The results are shown in Table 1.

EXAMPLE 2
Synthesis of CNP Derivatives

The peptides of the present invention were all prepared by the solid-phase method with a peptide synthesizer Model 431 of Applied Biosystems, Inc. As representative examples, the synthesis of compounds listed in Table 2 under 2 and 19 is shown below.

2-1: Compound No. 2 (See SEQ ID NO: 30)

Synthesis of H-Gly-Leu-Ser-Lys-Gly-Cys-Phe-Gly-Gly-Arg-Met-Asp-Arg-Ile-Gly-Ala-Gln-Ser-Glu-Leu-Glu-Cys-Asn-Ser-Phe-Arg-Tyr-OH (of disulfide type)

Starting with 0.7 g (0.5 mmol) of Boc-Tyr(Br-Z)-O-CH2-PAM resin, removal of Boc with 60% TFA, neutralization with DIEA, and condensation of protected amino acids with DCC/HOBt were repeated sequentially to obtain ca. 2.1 g of a protected peptide resin. The resin was treated with HF (17 ml) at $-2°$ C. for 60 min in the presence of para-cresol (3 ml). The free peptide was extracted with 50 ml of TFA and thereafter concentrated, followed by addition of ether to obtain 800 ml of a crude peptide. This peptide was dissolved in 32 g of urea-saturated water and added dropwise, with stirring, to urea-saturated water (288 ml, pH 7.4) containing potassium ferricyanide (147 mg, 44.8 μmol). After the end of the addition, the reaction solution was adjusted to pH 5 with acetic acid and loaded on a linked column of AG3-X4A (10 ml, Cl-form) and HP-20 (150 ml) that were equilibrated with 1N AcOH. After washing with 1N AcOH (500 ml), the peptide adsorbed on HP-20 was eluted with 80% CH3CN/1N AcOH. The fractions containing the desired peptide were concentrated and freeze-dried to obtain a crude cyclic peptide (750 mg).

Subsequently, the crude peptide was loaded on an ion-exchange column (CM-2SW, $2^\phi \times 15$ cm) equilibrated with water and the peptide was eluted by a 60-min linear gradient from water to 0.5M NH4OAc (pH 7.2). The principal fractions were collected, loaded on a reverse-phase C18 column (YMC-Pack D-ODS, $2^\phi \times 25$ cm) initialized with 0.1% TFA, and thereafter subjected to a 60-min linear gradient from 30% CH3CN/0.1% TFA to 60% CH3CN/0.1% TFA for elution at 10 ml/min. Fractions having a purity of at least 97% were collected and freeze-dried to obtain 150 mg of the end compound (2). All other derivatives excepting compound No. 19 were prepared in the manner described above.

2-2: Compound No. 19 (See SEQ ID NO: 31)

Synthesis of H-Gly-Leu-Ser-Lys-Gly-Cys(Me)-Phe-Gly-Leu-Lys-Leu-Asp-Arg-Ile-Gly-Ser-Met-Ser-Gly-Leu-Gly-Cys(Me)-OH Dithiothreitol (10 ml) was added to an aqueous solution (5 ml) of CNP (6.0 mg) and the resulting solution was adjusted to pH 8.5 with 10% aqueous ammonia, followed by standing at room temperature for 30 min. The reaction solution was loaded on a reverse-phase C18 column (YMC-Pack D-ODS, $2^\phi \times 25$ cm) and the desired peptide was isolated by CH3CN gradient elution in accordance with the procedure described in Example 1 under 1-1, and the isolated peptide was freeze-dried to obtain 5.7 mg (2.6 μmol) of reduced CNP. It was then dissolved in water (3 ml) and an acetonitrile solution (0.5 ml) containing 1.6 mg (7.3 μmol) of methyl 4-nitrobenzenesulfonate was added to the resulting aqueous solution and the mixture was left to stand at room temperature for 2 h. After verifying the loss of the starting material by HPLC, the peptide was separated on a reverse-phase C18 column to obtain 4.5 mg of the end compound (19).

As for the physiological activities of CNP, it was for the first time found by the present inventors that CNP had a strong cell growth suppressing activity with respect to vascular smooth muscle cells.

This action was found to be 10 times as strong as that of α-hANP. It was also found that a positive correlation holds between the intensity of that action and the concentration of intracellular cGMP.

Then, as for the correlation between the structure and activity of CNP, the present inventors found that the minimum activity structure for the cGMP producing activity of CNP was cyclic CNP (6–23) 5. It was also found that Leu-Lys-Leu, or the sequence of positions from 9 to 11 of CNP-22 as the primary amino acid sequence of the endocyclic domain of CNP, was important for the development of the cGMP producing activity of CNP.

Further, as regards the synthesis of novel CNP derivatives, the present inventors found that CNP derivatives exhibiting a stronger cGMP producing activity than CNP-22 or α-hANP could be constructed by replacing part of the amino acid residues in CNP-22, CNP (6–22) and [Leu10, Lys11, Leu12] α-hANP (7–28) with unusual amino acid (non-native type) residues.

On the basis of these findings, CNP and its derivatives that exhibit a strong cGMP producing activity and cell growth suppressing activity against vascular smooth muscle cells are anticipated to have utility as very effective therapeutics or preventives against diseases such as restenosis and arteriosclerosis that are caused by the abnormal growth of vascular smooth muscle cells. In this connection, it should be noted that among the derivatives synthesized in accordance with the present invention that contain unusual amino acid (non-native type) residues would probably exhibit resistance to proteases in the living body (in blood and on the surface of cells) upon administration in vivo. Therefore, those derivatives, even if they have a lower cGMP producing activity than CNP-22 or α-hANP, would be characterized by a longer blood half-life than CNP analogs free from unusual amino acids, and, from this viewpoint, too, those derivatives are anticipated to have industrial utility.

---

What is claimed is:

1. A novel peptide represented by the general formula:

(A)-(B)-(C)-Gly-(D)-(E)-(F)-Asp—Arg—Ile—Gly-(G)-(H)-
        :
        : . . . . . . . . . . . .
        :
Ser—Gly—Leu—Gly-(B)-(I)

and a physiologically acceptable acid addition salt thereof:
where (A) represents H-, H-Gly, H-Lys-Gly, H-Ser-Lys-Gly, H-Leu-Ser-Lys-Gly, H-Gly-Leu-Ser-Lys-Gly, H-Ser, H-Ser-Ser, H-Arg-Ser-Ser, H-Arg-Arg-Ser-Ser, H-Leu-Arg-Arg-Ser-Ser, H-Ser-Leu-Arg-Arg-Ser-Ser;
(B) represents H-Cys;
(C) represents Phe, pCl-Phe, pF-Phe, or Cha;
(D) represents Ile, Val or Leu;
(E) represents Lys;
(F) represents Leu;
(G) represents Ser or Ala;
(H) represents Met or Gln;
(I) represents —OH, -Asn-OH, -Asn-Ser-OH, -Asn-Ser-Phe-OH, -Asn-Ser-Phe-Arg-OH or -Asn-Ser-Phe-Arg-Tyr-OH; and
the symbol " . . . " represents a disulfide bond; provided that CNP-22 is excluded from the scope of that general formula.

2. A composition for suppressing the growth of vascular smooth muscle cells that comprises at least one CNP analog derivative as an effective ingredient, and a pharmaceutically acceptable carrier.

3. A method for suppressing the growth of vascular smooth muscle cells wherein a composition comprising at least one CNP analog derivative is administered.

4. A method for treating a disease caused by the abnormal growth of vascular smooth muscle cells, which comprises administering to a patient in need of such treatment a pharmaceutically effective amount of a CNP analog derivative.

5. The method according to claim 4, wherein the disease is restenosis of blood vessels or arteriosclerosis.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser Leu Arg Arg Ser Ser Cys Phe Gly Gly Arg Met Asp Arg Ile Gly
1               5                   10                  15
Ala Gln Ser Gly Leu Gly Cys Asn Ser Phe Arg Tyr
            20                  25
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Gly Leu Ser Lys Gly Cys Phe Gly Leu Lys Leu Asp Arg Ile Gly Ser
1               5                   10                  15
Met Ser Gly Leu Gly Cys
            20
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ser Leu Arg Arg Ser Ser Cys Phe Gly Gly Arg Met Asp Arg Ile Gly
1               5                   10                  15
Ala Gln Ser Gly Leu Gly Cys
            20
```

( 2 ) INFORMATION FOR SEQ ID NO:4:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gly Leu Ser Lys Gly Cys Phe Gly Gly Arg Met Asp Arg Ile Gly Ala
1               5                   10                  15
Gln Ser Gly Leu Gly Cys Asn Ser Phe Arg Tyr
            20                  25
```

( 2 ) INFORMATION FOR SEQ ID NO:5:

( i ) SEQUENCE CHARACTERISTICS:
        ( A ) LENGTH: 27 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:5:

Gly Leu Ser Lys Gly Cys Phe Gly Leu Lys Leu Asp Arg Ile Gly Ser
1               5                   10                  15

Met Ser Gly Leu Gly Cys Asn Ser Phe Arg Tyr
            20                  25

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ser Leu Arg Arg Ser Ser Cys Phe Gly Leu Lys Leu Asp Arg Ile Gly
1               5                   10                  15

Ser Met Ser Gly Leu Gly Cys
            20

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Cys Phe Gly Leu Lys Leu Asp Arg Ile Gly Ser Met Ser Gly Leu Gly
1               5                   10                  15

Cys (2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Gly Leu Ser Lys Gly Cys Phe Gly Gly Lys Leu Asp Arg Ile Gly Ser
1               5                   10                  15

Met Ser Gly Leu Gly Cys
            20

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gly Leu Ser Lys Gly Cys Phe Gly Leu Arg Leu Asp Arg Ile Gly Ser

Met Ser Gly Leu Gly Cys
              20

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Leu Ser Lys Gly Cys Phe Gly Leu Lys Met Asp Arg Ile Gly Ser
1               5                   10                  15

Met Ser Gly Leu Gly Cys
              20

(2) INFORMATION FOR SEQ ID NO:11:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Gly Leu Ser Lys Gly Cys Phe Gly Leu Lys Leu Asp Arg Ile Gly Ala
1               5                   10                  15

Met Ser Gly Leu Gly Cys
              20

(2) INFORMATION FOR SEQ ID NO:12:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Gly Leu Ser Lys Gly Cys Phe Gly Leu Lys Leu Asp Arg Ile Gly Ser
1               5                   10                  15

Gln Ser Gly Leu Gly Cys
              20

(2) INFORMATION FOR SEQ ID NO:13:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Gly Leu Ser Lys Gly Cys Phe Gly Gly Lys Met Asp Arg Ile Gly Ser
1               5                   10                  15

Met Ser Gly Leu Gly Cys
              20

( 2 ) INFORMATION FOR SEQ ID NO:14:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Gly Leu Ser Lys Gly Cys Phe Gly Leu Arg Met Asp Arg Ile Gly Ser
 1               5                   10                  15
Met Ser Gly Leu Gly Cys
            20
```

( 2 ) INFORMATION FOR SEQ ID NO:15:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Gly Leu Ser Lys Gly Cys Phe Gly Gly Arg Leu Asp Arg Ile Gly Ser
 1               5                   10                  15
Met Ser Gly Leu Gly Cys
            20
```

( 2 ) INFORMATION FOR SEQ ID NO:16:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Gly Leu Ser Lys Gly Cys Phe Gly Gly Arg Met Asp Arg Ile Gly Ser
 1               5                   10                  15
Met Ser Gly Leu Gly Cys
            20
```

( 2 ) INFORMATION FOR SEQ ID NO:17:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Ser Leu Arg Arg Ser Ser Cys Phe Gly Leu Lys Leu Asp Arg Ile Gly
 1               5                   10                  15
Ala Gln Ser Gly Leu Gly Cys Asn Ser Phe Arg Tyr
            20                  25
```

( 2 ) INFORMATION FOR SEQ ID NO:18:

( i ) SEQUENCE CHARACTERISTICS:
        ( A ) LENGTH: 22 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:18:

Gly Leu Ser Lys Gly Cys Xaa Gly Leu Lys Leu Asp Arg Ile Gly Ser
1               5                   10                      15

Met Ser Gly Leu Gly Cys
            20

(2) INFORMATION FOR SEQ ID NO:19:

(i) SEQUENCE CHARACTERISTICS:
    (A) LENGTH: 17 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:19:

Xaa Phe Gly Leu Lys Leu Asp Arg Ile Gly Ser Met Ser Gly Leu Gly
1               5                   10                      15

Cys (2) INFORMATION FOR SEQ ID NO:20:

(i) SEQUENCE CHARACTERISTICS:
    (A) LENGTH: 17 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:20:

Xaa Xaa Gly Leu Lys Leu Asp Arg Ile Gly Ser Met Ser Gly Leu Gly
1               5                   10                      15

Cys (2) INFORMATION FOR SEQ ID NO:21:

(i) SEQUENCE CHARACTERISTICS:
    (A) LENGTH: 22 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:21:

Gly Leu Ser Lys Gly Xaa Phe Gly Leu Lys Leu Asp Arg Ile Gly Ser
1               5                   10                      15

Met Ser Gly Leu Gly Xaa
            20

(2) INFORMATION FOR SEQ ID NO:22:

(i) SEQUENCE CHARACTERISTICS:
    (A) LENGTH: 22 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:22:

Gly Leu Ser Lys Gly Cys Phe Gly Ile Lys Leu Asp Arg Ile Gly Ser
1               5                   10                      15

Met  Ser  Gly  Leu  Gly  Cys
              20

( 2 ) INFORMATION FOR SEQ ID NO:23:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Gly  Leu  Ser  Lys  Gly  Cys  Phe  Gly  Val  Lys  Leu  Asp  Arg  Ile  Gly  Ser
1                 5                           10                          15

Met  Ser  Gly  Leu  Gly  Cys
              20

( 2 ) INFORMATION FOR SEQ ID NO:24:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Gly  Leu  Ser  Lys  Gly  Cys  Phe  Gly  Xaa  Lys  Leu  Asp  Arg  Ile  Gly  Ser
1                 5                           10                          15

Met  Ser  Gly  Leu  Gly  Cys
              20

( 2 ) INFORMATION FOR SEQ ID NO:25:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Gly  Leu  Ser  Lys  Gly  Cys  Phe  Gly  Xaa  Lys  Leu  Asp  Arg  Ile  Gly  Ser
1                 5                           10                          15

Met  Ser  Gly  Leu  Gly  Cys
              20

( 2 ) INFORMATION FOR SEQ ID NO:26:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Cys  Xaa  Gly  Leu  Lys  Leu  Asp  Arg  Ile  Gly  Ala  Gln  Ser  Gly  Leu  Gly
1                 5                           10                          15

Cys  Asn  Ser  Phe  Arg  Tyr
              20

( 2 ) INFORMATION FOR SEQ ID NO:27:

( i ) SEQUENCE CHARACTERISTICS:
   ( A ) LENGTH: 22 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:27:

Cys Xaa Gly Leu Lys Leu Asp Arg Ile Gly Ala Gln Ser Gly Leu Gly
1               5                   10                  15

Cys Asn Ser Phe Arg Tyr
            20

( 2 ) INFORMATION FOR SEQ ID NO:28:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:28:

Cys Xaa Gly Leu Lys Leu Asp Arg Ile Gly Ala Gln Ser Gly Leu Gly
1               5                   10                  15

Cys Asn Ser Phe Arg Tyr
            20

( 2 ) INFORMATION FOR SEQ ID NO:29:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

Cys Xaa Gly Leu Lys Leu Asp Arg Ile Gly Ala Gln Ser Gly Leu Gly
1               5                   10                  15

Cys Asn Ser Phe Arg Tyr
            20

( 2 ) INFORMATION FOR SEQ ID NO:30:

( i ) SEQUENCE CHARACTERISTICS:
      ( A ) LENGTH: 27 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

Gly Leu Ser Lys Gly Cys Phe Gly Gly Arg Met Asp Arg Ile Gly Ala
1               5                   10                  15

Gln Ser Glu Leu Glu Cys Asn Ser Phe Arg Tyr
            20                  25

( 2 ) INFORMATION FOR SEQ ID NO:31:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear (i i) MOLECULE TYPE: peptide (x i) SEQUENCE DESCRIPTION: SEQ ID NO:31:

```
Gly Leu Ser Lys Gly Cys Phe Gly Leu Lys Leu Asp Arg Ile Gly Ser
 1               5                  10                      15
Met Ser Gly Leu Gly Cys
             20
```

(2) INFORMATION FOR SEQ ID NO:32:

(i) SEQUENCE CHARACTERISTICS:
        (A) LENGTH: 19 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:32:

```
Xaa Xaa Xaa Gly Xaa Xaa Xaa Asp Arg Ile Gly Xaa Xaa Ser Gly Leu
 1               5                  10                      15
Gly Xaa Xaa
```

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:33:

```
Leu Ser Lys Gly
 1
```

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:34:

```
Gly Leu Ser Leu Gly
 1               5
```

(2) INFORMATION FOR SEQ ID NO:35:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:35:

```
Arg Arg Ser Ser
 1
```

(2) INFORMATION FOR SEQ ID NO:36:

(i) SEQUENCE CHARACTERISTICS:
        (A) LENGTH: 5 amino acids ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

Leu Arg Arg Ser Ser
1               5

( 2 ) INFORMATION FOR SEQ ID NO:37:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

Ser Leu Arg Arg Ser Ser
1               5

( 2 ) INFORMATION FOR SEQ ID NO:38:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

Asn Ser Phe Arg
1

( 2 ) INFORMATION FOR SEQ ID NO:39:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

Asn Ser Phe Arg Tyr
1               5

( 2 ) INFORMATION FOR SEQ ID NO:40:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

( 2 ) INFORMATION FOR SEQ ID NO:41:

( i ) SEQUENCE CHARACTERISTICS:

(A) LENGTH: 32 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

```
Ser Pro Lys Met Val Gln Gly Ser Gly Cys Phe Gly Arg Lys Met Asp
1               5                   10                  15
Arg Ile Ser Ser Ser Ser Gly Leu Gly Cys Lys Val Leu Arg Arg His
            20                  25                  30
```

(2) INFORMATION FOR SEQ ID NO:42:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:42:

```
Gly Leu Ser Lys Gly Cys Phe Gly Leu Lys Leu Asp Arg Ile Gly Ser
1               5                   10                  15
Met Ser Gly Leu Gly Cys
            20
```